(12) United States Patent
Woo et al.

(10) Patent No.: US 10,538,504 B2
(45) Date of Patent: Jan. 21, 2020

(54) PREPARATION METHOD OF INTERMEDIATE FOR OXAZOLIDINONE DERIVATIVE

(71) Applicant: ST PHARM CO., LTD., Gyeonggi-do (KR)

(72) Inventors: Seok Hun Woo, Gyeonggi-do (KR); YunHee Choi, Gyeonggi-do (KR); Hong Jun Kim, Gyeonggi-do (KR); Sun Ki Chang, Gyeonggi-do (KR); Geun Jho Lim, Seoul (KR)

(73) Assignee: ST PHARM CO., LTD. (KR)

( * ) Notice: Subject to any disclaimer, the term of this patent is extended or adjusted under 35 U.S.C. 154(b) by 0 days.

(21) Appl. No.: 16/060,655

(22) PCT Filed: Dec. 9, 2016

(86) PCT No.: PCT/KR2016/014467
§ 371 (c)(1),
(2) Date: Jun. 8, 2018

(87) PCT Pub. No.: WO2017/099530
PCT Pub. Date: Jun. 15, 2017

(65) Prior Publication Data
US 2018/0346443 A1 Dec. 6, 2018

(30) Foreign Application Priority Data
Dec. 11, 2015 (KR) .................. 10-2015-0177169

(51) Int. Cl.
*C07D 401/04* (2006.01)
(52) U.S. Cl.
CPC .................. *C07D 401/04* (2013.01)
(58) Field of Classification Search
CPC .................................................. C07D 401/04
USPC .................................................. 546/268.4
See application file for complete search history.

(56) References Cited

U.S. PATENT DOCUMENTS 7,498,350 B2 * 3/2009 Gravestock .......... C07D 413/14
514/340
2004/0033970 A1 2/2004 Clark et al.

FOREIGN PATENT DOCUMENTS

| KR | 1020050061271 A | 8/2008 | |
| KR | 1020110071107 A | 11/2016 | |
| WO | WO-2004048350 A2 * | 6/2004 | .......... C07D 413/14 |
| WO | WO2004/056819 A1 | 7/2004 | |
| WO | 2006038100 A1 | 4/2006 | |
| WO | WO2010/042887 A2 | 4/2010 | |

OTHER PUBLICATIONS

International Search report for corresponding International Application No. PCT/KR2016/014467 filed on Dec. 9, 2016; Report dated Mar. 17, 2017.
Jo, Y. W., et al., "Synthesis and antibacterial activity of oxazolidinones containing pyridine substituted with heteroaromatic ring", Bioorganic & Medicinal Chemistry, 2004, vol. 12, No. 22, pp. 5909-5915.
Im, W. B., et al., "Discovery of torezolid as a novel 5-hydroxymethyl-oxazolidinone antibacterial agent", European Journal of Medicinal Chemistry, 2011, vol. 46, No. 4, pp. 1027-1039.
European Search report for Application No. 16873395.4; dated Jun. 19, 2019.
William Many et al., "Copper Catalyzed Assembly of N-Aryloxazolidinones: Synthesis of Linezolid, Tedizolid, and Rivaroxaban", European Journal of Organic Chemistry, 2016, pp. 1305-1313.

* cited by examiner

*Primary Examiner* — Rita J Desai
(74) *Attorney, Agent, or Firm* — Miller, Matthias & Hull LLP

(57) ABSTRACT

Disclosed is a method of preparing an intermediate for an oxazolidinone derivative, which enables 5-bromo-2-(2-methyl-2H-tetrazol-5-yl)pyridine to be produced at high yield and high purity, thus exhibiting high preparation efficiency under optimal processing conditions and making it suitable for industrial mass production.

17 Claims, No Drawings

PREPARATION METHOD OF INTERMEDIATE FOR OXAZOLIDINONE DERIVATIVE

CROSS-REFERENCE TO RELATED APPLICATIONS

This patent application is a 35 U.S.C. § 371 U.S. national stage filing of International Application No. PCT/KR2016/014467, filed in the Korean Receiving Office on Dec. 9, 2016, and claims priority to, and the benefit of, Korean Patent Application No. 10-2015-0177169, filed Dec. 11, 2015, the disclosures of which are hereby incorporated by reference in their entireties.

TECHNICAL FIELD

The present invention relates to a method of preparing an intermediate for an oxazolidinone derivative.

BACKGROUND ART

Tedizolid is a compound having an oxazolidinone structure, and has the chemical name "(5R)-3-{3-fluoro-4-[6-(2-methyl-2H-tetrazol-5-yl)pyridin-3-yl]phenyl}-5-(hydroxymethyl)-1,3-oxazolidin-2-one". This tedizolid is an oxazolidinone-based derivative compound (disclosed in Korean Patent Application Publication No. 10-2005-0061271) that is useful as a disinfecting agent, and is sold in the form of an oral formulation and an injectable formulation under the trade name of SIVEXTRO, with the permission of the U.S. Food and Drug Administration.

Korean Patent Application Publication No. 10-2005-0061271 discloses a method of preparing an intermediate for an oxazolidinone derivative, as shown in Scheme 1 below.

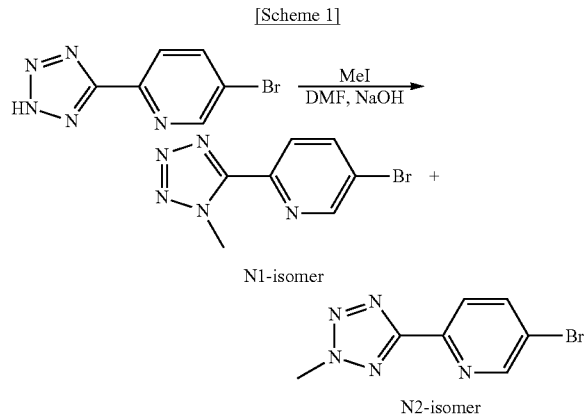

In the preparation procedures of Scheme 1, however, the methylation of tetrazole is not selective, undesirably producing tetrazole in which the methyl group is added to a different position.

This is because the NH bonding of tetrazole is present in two tautomer forms. Hence, when the methyl group is added to tetrazole, two kinds of compounds, namely 1,5-disubstituted tetrazole and 2,5-disubstituted tetrazole, are formed.

The methylation of tetrazole in this way is not suitable for industrial use because of the low yield and low selectivity to desired compounds, and also suffers from high production costs.

Furthermore, dimethyl sulfate, diazomethane, or trimethylsilyl diazomethane, useful for the methylation of tetrazole, is highly toxic, highly explosive, and expensive, and is thus inappropriate for industrial mass production.

DISCLOSURE

Technical Problem

Accordingly, the present invention has been made keeping in mind the above problems encountered in the related art, and the present invention is intended to provide a method of preparing an intermediate for an oxazolidinone derivative, namely 5-bromo-2-(2-methyl-2H-tetrazol-5-yl)pyridine, at high yield and high purity from 5-bromo-2-(2H-tetrazol-5-yl)pyridine.

Technical Solution

The present invention provides a method of preparing the compound represented by Chemical Formula 1 below, comprising reacting the compound represented by Chemical Formula 2 below with a methylating agent in the presence of a solvent and a base, wherein the solvent is a solvent mixture of a polar aprotic solvent and a hydrocarbon chloride solvent or a polar protic solvent.

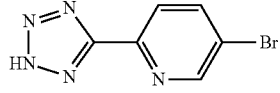

[Chemical Formula 2]

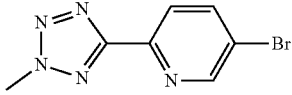

[Chemical Formula 1]

The compound represented by Chemical Formula 2 is a compound having the chemical name of 5-bromo-2-(2H-tetrazol-5-yl)pyridine, and the compound represented by Chemical Formula 1 is a compound having the chemical name of 5-bromo-2-(2-methyl-2H-tetrazol-5-yl)pyridine, and a structural difference between these two compounds is the presence or absence of the methyl group that is substituted in the tetrazole ring.

The method of the invention is a methylation reaction, in which a methyl group is added to the nitrogen at Position 2 on the tetrazole ring of the compound represented by Chemical Formula 2 in place of hydrogen.

The methylation reaction of the invention is preferably carried out using a solvent mixture comprising a polar aprotic solvent and a hydrocarbon chloride solvent or a polar protic solvent.

The polar aprotic solvent may include, but is not limited to, at least one selected from the group consisting of N,N-dimethyl formamide, tetrahydrofuran, ethyl acetate, chloroform, 1,2-dichloroethane, 1,4-dioxane, ethyl ether, diisopropyl ether, diethylene glycol dimethyl ether, acetone, 2-butanone, cyclohexanone, dimethyl sulfoxide, N,N-dimethyl acetamide, and mixtures thereof.

The hydrocarbon chloride solvent is preferably methylene chloride.

The polar protic solvent may include, but is not limited to, at least one selected from the group consisting of water, methanol, ethanol, isopropanol, butanol, nitromethane, acetic acid, and mixtures thereof.

Preferably, the solvent mixture of the invention is a solvent mixture of N,N-dimethyl formamide and methylene chloride, a solvent mixture of N,N-dimethyl formamide and methanol, or a solvent mixture of N,N-dimethyl formamide and ethanol.

The solvent mixture of N,N-dimethyl formamide and methylene chloride comprises N,N-dimethyl formamide and methylene chloride at a volume ratio of 1:1 to 50, preferably 1:1 to 9, and more preferably 1:9.

The solvent mixture of N,N-dimethyl formamide and methanol comprises N,N-dimethyl formamide and methanol at a volume ratio of 1:1 to 50, preferably 1:1 to 9, and more preferably 3:7.

The solvent mixture of N,N-dimethyl formamide and ethanol comprises N,N-dimethyl formamide and ethanol at a volume ratio of 1:1 to 50, preferably 1:1 to 9, and more preferably 1:1 or 3:7.

The base, which is used in the methylation reaction of the invention, may be an inorganic base or an organic base, and preferably includes, but is not limited to, at least one selected from the group consisting of lithium hydroxide (LiOH), sodium hydroxide (NaOH), sodium carbonate ($Na_2CO_3$), potassium carbonate ($K_2CO_3$), cesium carbonate ($Cs_2CO_3$), calcium carbonate ($CaCO_3$), calcium hydroxide ($Ca(OH)_2$), iron hydroxide (FeO(OH)), potassium hydroxide (KOH), magnesium hydroxide ($Mg(OH)_2$), pyridine, piperidine, triethylamine, N,N-diisopropylethylamine (DIEA), and mixtures thereof.

Preferably, the base used in the methylation reaction of the invention is calcium hydroxide ($Ca(OH)_2$).

Preferably, the base is used in an amount of 0.3 to 7.0 equivalents relative to 1 equivalent of the compound represented by Chemical Formula 2, and more preferably, 0.4 to 1.2 equivalents relative to 1 equivalent of the compound represented by Chemical Formula 2, in order to attain higher selectivity and yield.

The methylating agent used in the methylation reaction of the invention is preferably iodomethane.

Also, the methylation reaction of the invention may be carried out at 0 to 100° C., and is preferably carried out at 20 to 40° C. in order to attain higher selectivity and yield.

In the method of the invention, the compound represented by Chemical Formula 2 may be formed into the compound represented by Chemical Formula 1 at a high yield of 65% or more and a high purity of 99% or more through purification, with a selectivity at an N2/N1 ratio of at least 75/25, preferably at least 80/20, and more preferably at least 85/15.

In the method of the invention, a methyl group may be selectively added to the nitrogen at Position 2 on the tetrazole ring of the compound represented by Chemical Formula 2, thereby preparing the compound represented by Chemical Formula 1 at high yield and high purity with very high selectivity. Thus, the method of the invention may be easily applied to industrial mass production.

Also, the compound represented by Chemical Formula 2 is preferably prepared by reacting the compound represented by Chemical Formula 3 below with an alkali metal azide using a pyridine solvent in the presence of zinc chloride.

[Chemical Formula 3]

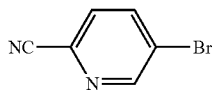

The alkali metal azide may include, but is not limited to, lithium azide, sodium azide, potassium azide, or cerium azide.

When the compound of Chemical Formula 2 is prepared from the compound of Chemical Formula 3 in this way, ammonium chloride, which is typically used in the process of preparing tetrazole, is not used, and thus the generation of toxic gases may be prevented, making the process of the invention environmentally friendly. The use of zinc chloride enables tetrazole, namely the compound of Chemical Formula 2, to be produced at higher yield and purity.

Also, the method of preparing the compound represented by Chemical Formula 1 may further comprise crystallizing the compound of Chemical Formula 1 using a crystallization solvent.

The compound of Chemical Formula 1 resulting from the methylation reaction may be purified through crystallization with the crystallization solvent.

The crystallization solvent may be at least one selected from the group consisting of a polar protic solvent, a polar aprotic solvent, $C_{4-11}$ ether, $C_{4-8}$ alkane, $C_{1-4}$ lower alcohol, and mixtures thereof. Preferably useful as the crystallization solvent is acetone.

Advantageous Effects

According to the present invention, the method enables an intermediate for an oxazolidinone derivative, namely 5-bromo-2-(2-methyl-2H-tetrazol-5-yl)pyridine, to be prepared at high yield and high purity from 5-bromo-2-(2H-tetrazol-5-yl)pyridine, thus exhibiting high preparation efficiency under optimal processing conditions and making it suitable for industrial mass production.

MODE FOR INVENTION

A better understanding of the present invention may be obtained through the following examples which are set forth to illustrate, but are not to be construed as limiting the present invention.

REFERENCE EXAMPLE: REAGENT AND INSTRUMENT

Unless otherwise stated, the following reagents and instruments were purchased from Sigma-Aldrich Korea, HPLC was performed using a 1200 Series model available from Agilent Technologies, and $^1H$ NMR was measured using a Bruker NMR 400 MHz Spectrometer. The purity was measured based on the area % of HPLC.

| HPLC Conditions | |
|---|---|
| Parameter | Conditions/Setting |
| HPLC system | Reverse phase |
| Column | Waters Sunfire C18, 3.5 μm, 4.6*150 mm |
| Column temperature | Room temperature |
| Automatic sampler temperature | Room temperature |
| Detection | UV at 254 nm |
| Mobile phase A | 0.1% TFA in water |
| Mobile phase B | 0.1% TFA in AN |

| Gradient | | |
|---|---|---|
| Time (min) | Mobile phase A (%) | Mobile phase B (%) |
| 0.00 | 100 | 0 |

-continued

| HPLC Conditions | | |
|---|---|---|
| 2.0 | 100 | 0 |
| 20.0 | 0 | 100 |
| 21.0 | 100 | 0 |
| 31.0 | 100 | 0 |

| | |
|---|---|
| Flow rate | 1.0 mL/min |
| Injection volume | 10 μL |
| Data collection time | 20 min |

Example 1: Preparation of 5-bromo-2-(2H-tetrazol-5-yl)pyridine

Pyridine (40.0 mL, 4.0 v/w) was placed in a reactor, and zinc chloride (11.2 g, 81.9 mmol) was added dropwise at 40° C. or less. Thereafter, sodium azide (8.90 g, 137 mmol) and 5-bromo-2-cyanopyridine (10.0 g, 54.6 mmol) were added into the reactor, and the reaction mixture was stirred to reflux at 120° C. for 2 hr. After the termination of the reaction, the reaction product was cooled to room temperature, added with purified water (200 mL, 20.0 v/w), stirred at room temperature for 1 hr, filtered, and washed with purified water (200 mL, 20.0 v/w). The filtered solid was added with a 6 N hydrochloric acid aqueous solution (200 mL, 20.0 v/w) and then stirred at room temperature for 2 hr. The reaction product was filtered, washed with purified water (200 mL, 20.0 v/w), and concentrated under reduced pressure, thus yielding a desired white compound. Yield (11.34 g, 91.8%), Purity 99.4%

5-bromo-2-(2H-tetrazol-5-yl)pyridine:
$^1$H NMRδ (DMSO-d6, ppm) 8.95 (d,1H), 8.35 (dd,1H), 8.17 (d, 1H)

Example 2: Preparation of 5-bromo-2-(2-methyl-2H-tetrazol-5-yl)pyridine

The 5-bromo-2-(2H-tetrazol-5-yl)pyridine (20.0 g, 88.4 mmol) prepared in Example 1 was added with 20.0 mL of N,N-dimethyl formamide and 180.0 mL of methylene chloride and then further added with calcium hydroxide (3.94 g, 53.0 mmol), after which iodomethane (33.0 mL, 530.4 mmol) was slowly added dropwise thereto at 0° C. Thereafter, the reaction solution was warmed to 40° C. and stirred for 24 hr. After the termination of the reaction, the reaction solution was added with water, thus extracting an organic layer. The extracted organic layer was washed with saline and further extracted. The resulting organic layer was added with 300.0 mL of a 6 N hydrochloric acid aqueous solution to thus extract an aqueous layer, after which the separated organic layer was added with 60.0 mL of a 6 N hydrochloric acid aqueous solution, so that the aqueous layer was further extracted. Extraction was performed using HPLC until the amount of N1 was less than 5%. The separated aqueous layer was collected, and the pH thereof was adjusted to 10.6 at 40° C. or less using a 50% sodium hydroxide aqueous solution. The produced solid was filtered, washed with water, and concentrated under reduced pressure, thus obtaining a desired compound. Yield (16.2 g, 70.5%), N2/N1 ratio % (98/2)

Examples 3 to 14: Preparation of 5-bromo-2-(2-methyl-2H-tetrazol-5-yl)pyridine The 5-bromo-2-(2-methyl-2H-tetrazol-5-yl)pyridine of Examples 3 to 14 was prepared from 5-bromo-2-(2H-tetrazol-5-yl)pyridine in the same manner as in Example 2, with the exception that the methylating agent, base, solvent, warming and stirring temperature and reaction temperature were changed as shown in Table 1 below. The results of the amount (%) of the starting material (5-bromo-2-(2H-tetrazol-5-yl)pyridine) remaining after the reaction and the N2/N1 ratio are shown in Table 2 below.

TABLE 1

| | Methylating agent | Base | Solvent | Temp. | Reaction time |
|---|---|---|---|---|---|
| Ex. 3 | MeI (7.0 eq) | NaOH (3.5 eq) | DMF/EtOH (1/1, 10 v/w) | RT | 30 hr |
| Ex. 4 | MeI (7.0 eq) | NaOH (3.5 eq) | DMF/MeOH (1/1, 10 v/w) | RT | 30 hr |
| Ex. 5 | MeI (7.0 eq) | Ca(OH)$_2$ (3.5 eq) | DMF/MC (3/7, 10 v/w) | RT | 24 hr |
| Ex. 6 | MeI (10.0 eq) | NaOH (3.5 eq) | DMF/MC (3/7, 10 v/w) | 40° C. | 24 hr |
| Ex. 7 | MeI (10.0 eq) | NaOH (3.5 eq) | DMF/EtOH (3/7, 10 v/w) | 40° C. | 22 hr |
| Ex. 8 | MeI (7.0 eq) | NaOH (1.0 eq) | DMF/MC (3/7, 10 v/w) | 40° C. | 24 hr |
| Ex. 9 | MeI (7.0 eq) | NaOH (2.0 eq) | DMF/MC (3/7, 10 v/w) | 40° C. | 23 hr |
| Ex. 10 | MeI (5.0 eq) | Ca(OH)$_2$ (0.5 eq) | DMF/MC (1/9, 10 v/w) | 40° C. | 30 hr |
| Ex. 11 | MeI (6.0 eq) | Ca(OH)$_2$ (0.6 eq) | DMF/MC (1/9, 10 v/w) | 40° C. | 22 hr |
| Ex. 12 | MeI (9.0 eq) | Ca(OH)$_2$ (0.6 eq) | DMF/MC (1/9, 10 v/w) | 40° C. | 22 hr |
| Ex. 13 | MeI (10.0 eq) | Ca(OH)$_2$ (1.0 eq) | DMF/MC (1/9, 10 v/w) | 40° C. | 24 hr |
| Ex. 14 | MeI (10.0 eq) | Ca(OH)$_2$ (3.5 eq) | DMF/MC (1/9, 10 v/w) | 40° C. | 24 hr |

(MeI: iodomethane, NaOH: sodium hydroxide, Ca(OH)$_2$: calcium hydroxide, DMF: N,N-dimethyl formamide, EtOH: ethanol, MeOH: methanol, MC: methylene chloride, eq: equivalent, RT: room temperature)

TABLE 2

| | Starting material % | N2/N1 Ratio |
|---|---|---|
| Ex. 3 | 5.03 | 79/21 |
| Ex. 4 | 7.13 | 75/25 |

TABLE 2-continued

| | Starting material % | N2/N1 Ratio |
|---|---|---|
| Ex. 5 | 0.14 | 77/23 |
| Ex. 6 | 4.05 | 82/18 |
| Ex. 7 | 8.57 | 79/21 |
| Ex. 8 | 2.51 | 75/25 |
| Ex. 9 | 0.51 | 81/19 |
| Ex. 10 | 0.20 | 89/11 |
| Ex. 11 | 0.09 | 89/11 |
| Ex. 12 | 0.44 | 88/12 |
| Ex. 13 | 1.25 | 88/12 |
| Ex. 14 | 0.83 | 85/15 |

(Starting material %: the amount (%) of 5-bromo-2-(2H-tetrazol-5-yl)pyridine remaining after methylation, N2/N1 Ratio: Ratio of compound in which methyl is added to Position 2 of tetrazole/compound in which methyl is added to Position 1 of tetrazole)

Example 15: Purification of 5-bromo-2-(2-methyl-2H-tetrazol-5-yl)pyridine 16.2 g of the dried 5-bromo-2-(2-methyl-2H-tetrazol-5-yl)pyridine of Example 2 was added with 48.6 mL of acetone, stirred to reflux for 1 hr, and cooled to room temperature to produce a solid, which was then filtered, washed with purified water, dewatered, and concentrated under reduced pressure. Yield (15.1 g, 65.7%, recovery efficiency 93.2%), Purity 99.3%

5-bromo-2-(2-methyl-2H-tetrazol-5-yl)pyridine:
$^1$H NMRδ (CDCl$_3$, ppm) 8.82 (dd,1H), 8.14 (dd,1H), 8.00 (dd,1H), 4.45 (s,3H)

The invention claimed is:

1. A method of preparing a compound represented by Chemical Formula 1 below, comprising reacting a compound represented by Chemical Formula 2 below with a methylating agent in presence of a solvent and a base, wherein the solvent is a solvent mixture of a polar aprotic solvent and a hydrocarbon chloride solvent or a polar protic solvent:

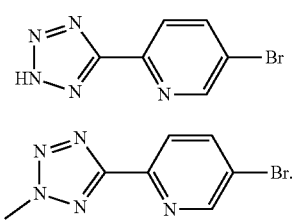

[Chemical Formula 2]

[Chemical Formula 1]

2. The method of claim 1, wherein the polar aprotic solvent is at least one selected from the group consisting of N,N-dimethyl formamide, tetrahydrofuran, ethyl acetate, chloroform, 1,2-dichloroethane, 1,4-dioxane, ethyl ether, diisopropyl ether, diethylene glycol dimethyl ether, acetone, 2-butanone, cyclohexanone, dimethyl sulfoxide, N,N-dimethyl acetamide, and mixtures thereof.

3. The method of claim 1, wherein the hydrocarbon chloride solvent is methylene chloride.

4. The method of claim 1, wherein the polar protic solvent is at least one selected from the group consisting of water, methanol, ethanol, isopropanol, butanol, nitromethane, acetic acid, and mixtures thereof.

5. The method of claim 1, wherein the solvent mixture is a solvent mixture of N,N-dimethyl formamide and methylene chloride, a solvent mixture of N,N-dimethyl formamide and methanol, or a solvent mixture of NN-dimethyl formamide and ethanol.

6. The method of claim 5, wherein the solvent mixture of N,N-dimethyl formamide and methylene chloride comprises N,N-dimethyl formamide and methylene chloride at a volume ratio of 1:1 to 50, the solvent mixture of NN-dimethyl formamide and methanol comprises N,N-dimethyl formamide and methanol at a volume ratio of 1:1 to 50, or the solvent mixture of N,N-dimethyl formamide and ethanol comprises N,N-dimethyl formamide and ethanol at a volume ratio of 1:1 to 50.

7. The method of claim 5, wherein the solvent mixture of N,N-dimethyl formamide and methylene chloride comprises N,N-dimethyl formamide and methylene chloride at a volume ratio of 1:1 to 9, the solvent mixture of NN-dimethyl formamide and methanol comprises NN-dimethyl formamide and methanol at a volume ratio of 1:1 to 9, or the solvent mixture of N,N-dimethyl formamide and ethanol comprises N,N-dimethyl formamide and ethanol at a volume ratio of 1:1 to 9.

8. The method of claim 1, wherein the base is at least one selected from the group consisting of lithium hydroxide (LiOH), sodium hydroxide (NaOH), sodium carbonate (Na$_2$CO$_3$), potassium carbonate (K$_2$CO$_3$), cesium carbonate (Cs$_2$CO$_3$), calcium carbonate (CaCO$_3$), calcium hydroxide (Ca(OH)$_2$), iron hydroxide (FeO(OH)), potassium hydroxide (KOH), magnesium hydroxide (Mg(OH)$_2$), pyridine, piperidine, triethylamine, N,N-diisopropylethylamine (DIEA), and mixtures thereof.

9. The method of claim 1, wherein the base is calcium hydroxide (Ca(OH)$_2$).

10. The method of claim 1, wherein the base is used in an amount of 0.3 to 7.0 equivalents relative to 1 equivalent of the compound represented by Chemical Formula 2.

11. The method of claim 1, wherein the methylating agent is iodomethane.

12. The method of claim 1, wherein the reacting is carried out at 0 to 100° C.

13. The method of claim 1, wherein the compound represented by Chemical Formula 2 is prepared by reacting a compound represented by Chemical Formula 3 below with an alkali metal azide using a pyridine solvent in presence of zinc chloride:

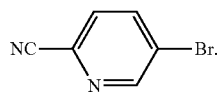

[Chemical Formula 3]

14. The method of claim 13, wherein the alkali metal azide is lithium azide, sodium azide, potassium azide, or cerium azide.

15. The method of any one of claims 1 to 14, further comprising crystallizing the compound of Chemical Formula 1 using a crystallization solvent.

16. The method of claim 15, wherein the crystallization solvent is at least one selected from the group consisting of a polar protic solvent, a polar aprotic solvent, C$_{4-11}$ ether, C$_{4-8}$ alkane, C$_{1-4}$ lower alcohol, and mixtures thereof.

17. The method of claim 16, wherein the crystallization solvent is acetone.

* * * * *